US006464718B1

(12) United States Patent
Miller et al.

(10) Patent No.: US 6,464,718 B1
(45) Date of Patent: *Oct. 15, 2002

(54) BALLOON CATHETER FOR STENT DELIVERY HAVING MICROCHANNELS AND METHOD

(75) Inventors: Jay F. Miller, Miramar; Edward J. Play, Weston, both of FL (US)

(73) Assignee: Cordis Corporation, Miami Lakes, FL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 120 days.

(21) Appl. No.: 09/193,035

(22) Filed: Nov. 16, 1998

(51) Int. Cl.[7] .................................................. A61F 2/06
(52) U.S. Cl. ...................... 623/1.11; 606/198; 606/192; 606/194
(58) Field of Search .......................... 606/194, 190–193, 606/197–198, 108, 111, 191; 623/1.11, 1.23, 1.27–1.29

(56) References Cited

U.S. PATENT DOCUMENTS

| 4,733,665 A | 3/1988 | Palmaz |
| 4,739,762 A | 4/1988 | Palmaz |
| 4,762,128 A | 8/1988 | Rosenbluth |
| 4,776,337 A | 10/1988 | Palmaz |
| 4,906,244 A | * 3/1990 | Pinchuk et al. ............. 606/194 |

(List continued on next page.)

FOREIGN PATENT DOCUMENTS

| EP | 0 442 657 A2 | 8/1991 |
| EP | 0 335 341 B1 | 3/1992 |
| EP | 0 707 837 A1 | 4/1996 |
| EP | 0 714 640 A1 | 6/1996 |
| EP | 0 409 929 B1 | 4/1997 |
| EP | 0 770 366 B1 | 5/1997 |
| EP | 0 778 010 A2 | 6/1997 |
| EP | 0 778 012 A2 | 6/1997 |
| EP | 0 779 062 A1 | 6/1997 |
| EP | 0 850 605 A2 | 7/1998 |
| EP | 0 855 171 A2 | 7/1998 |
| WO | WO 95/33422 | 12/1995 |
| WO | WO 97/21400 | 6/1997 |

*Primary Examiner*—Michael J. Milano
*Assistant Examiner*—Vy Q. Bui

(57) ABSTRACT

A balloon catheter and stent delivery system for medical treatment of a patient includes a balloon inflatable to an inflated shape having a cylindrical working portion, and a deflated shape that is temporarily reformed to enhance longitudinal retention of the stent while the catheter system is advanced or withdrawn. The balloon catheter provides for uniform expansion of the stent when the balloon is inflated. In addition, the balloon catheter system can be modified to initiate partial inflation of the proximal and distal ends of the stent, to further resist longitudinal motion of the stent during inflation, and to facilitate more effective tacking of the stent. One possible feature of the catheter system is that the balloon is pleated in a particular pattern when deflated, whereby the central balloon portion carrying the stent has a greater number of pleats than the pillow portions proximal and distal of the stent. Another possible feature is the formation of small channels that facilitate fluid communication from the proximal end of the balloon to the distal end, even when the balloon is deflated. The balloon may be formed to protrude partially outward among the stent interstices while in its deflated state, further enhancing stent position retention. The present invention also protects the leading or distal end of the stent during advancement, and protects the proximal end of the stent during any withdrawal of the catheter system.

4 Claims, 7 Drawing Sheets

U.S. PATENT DOCUMENTS

| | | |
|---|---|---|
| 4,950,227 A | 8/1990 | Savin et al. |
| 5,104,404 A * | 4/1992 | Wolff .......................... 623/1 |
| 5,108,416 A | 4/1992 | Ryan et al. |
| 5,242,399 A | 9/1993 | Lau et al. |
| 5,254,091 A | 10/1993 | Aliahmad et al. |
| 5,370,615 A | 12/1994 | Johnson |
| 5,395,390 A * | 3/1995 | Simon et al. ............... 606/198 |
| 5,403,341 A | 4/1995 | Solar |
| 5,409,495 A * | 4/1995 | Osborn ........................ 606/108 |
| 5,478,320 A | 12/1995 | Trotta |
| 5,484,411 A | 1/1996 | Inderbitzen et al. |
| 5,549,635 A | 8/1996 | Solar |
| 5,569,295 A | 10/1996 | Lam |
| 5,632,760 A | 5/1997 | Sheiban et al. |
| 5,645,789 A | 7/1997 | Roucher, Jr. |
| 5,658,311 A | 8/1997 | Baden |
| 5,672,169 A | 9/1997 | Verbeek |
| 5,695,498 A | 12/1997 | Tower |
| 5,746,745 A * | 5/1998 | Abele et al. ................. 606/108 |
| 5,792,106 A | 8/1998 | Mische |
| 5,792,172 A * | 8/1998 | Fischell et al. ............. 606/198 |
| 5,792,415 A | 8/1998 | Hijlkema |
| 5,810,871 A | 9/1998 | Tuckey et al. |
| 5,836,965 A | 11/1998 | Jendersee et al. |
| 5,913,871 A | 6/1999 | Werneth et al. |
| 5,935,135 A | 8/1999 | Bramfitt et al. |
| 5,968,069 A | 10/1999 | Dusbabek et al. |
| 5,971,990 A | 10/1999 | Venturelli |
| 6,027,510 A | 2/2000 | Alt |
| 6,056,906 A | 5/2000 | Werneth et al. |
| 6,063,092 A | 5/2000 | Shin |

\* cited by examiner

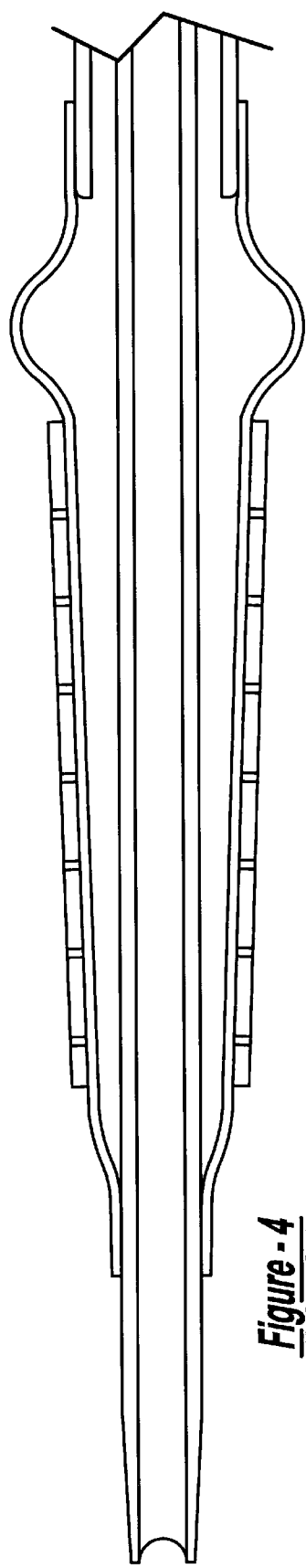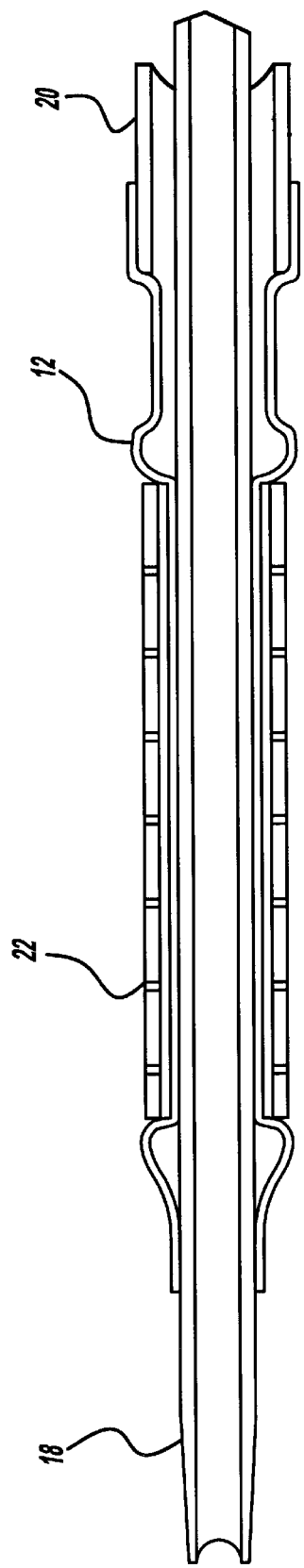

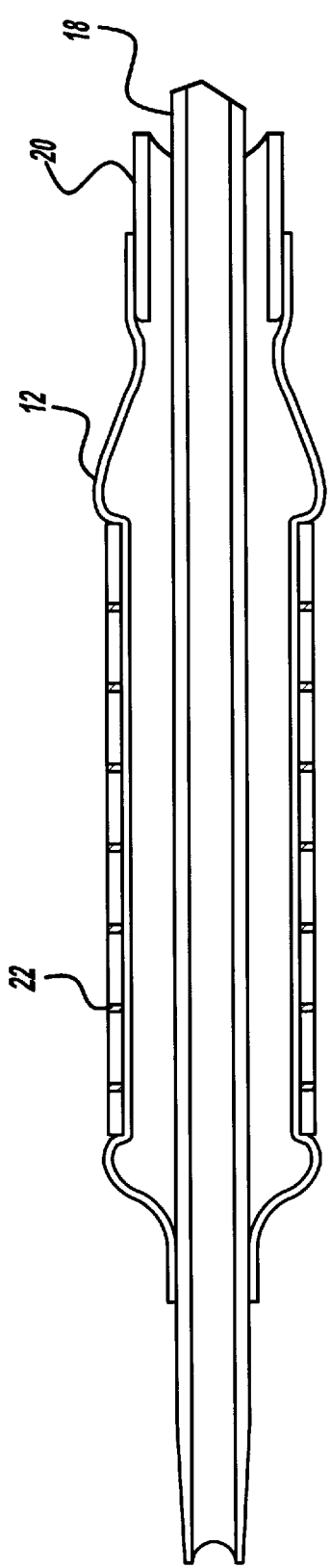
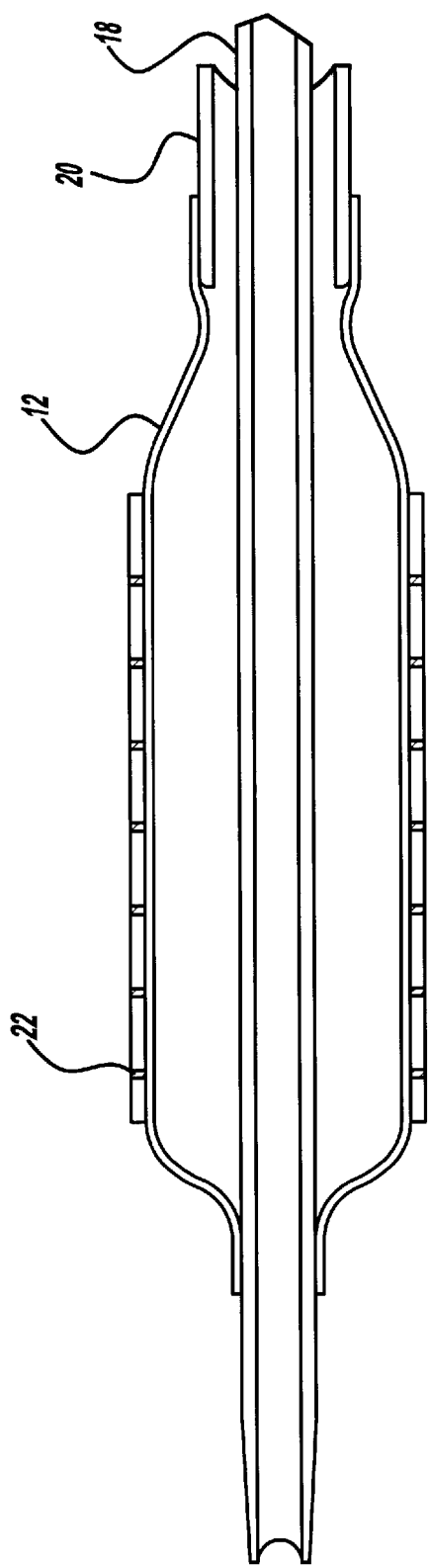
Figure - 6
Figure - 7

BALLOON CATHETER FOR STENT DELIVERY HAVING MICROCHANNELS AND METHOD

BACKGROUND AND SUMMARY OF THE INVENTION

1. Technical Background

The present invention relates generally to medical devices, and more particularly to a balloon catheter and stent delivery system.

2. Discussion

Balloon catheters are used in a variety of therapeutic applications, including intravascular catheters for procedures such as angioplasty. Nearly one million angioplasties were performed worldwide in 1997 to treat vascular disease, including coronary, neurological and peripheral blood vessels partially or totally blocked or narrowed by a stenosis. By way of example, the present invention will be described in relation to coronary and peripheral angioplasty treatments. However, it should be understood that the present invention relates to any balloon catheter and stent delivery system having enhanced stent retention, and is not limited to angioplasty.

Most balloon catheters have a relatively long and flexible tubular shaft defining one or more passages or lumens, and an inflatable balloon attached near one end of the shaft. This end of the catheter where the balloon is located is customarily referred to as the "distal" end, while the other end is called the "proximal" end. The balloon is connected to one of the lumens extending through the shaft for the purpose of selectively inflating and deflating the balloon. The other end of this inflation lumen leads to a hub coupling at the other end for connecting the shaft lumens to various equipment. Examples of this type of balloon catheter are shown in U.S. Pat. No. 5,304,197, entitled "Balloons For Medical Devices And Fabrication Thereof," issued to Pinchuk et al. on Apr. 19th, 1994, and also in U.S. Pat. No. 5,370,615, entitled "Balloons Catheter For Angioplasty," issued to Johnson on Dec. 6, 1994.

A common treatment method for using such a balloon catheter is to advance the catheter into the body of a patient, by directing the catheter distal end percutaneously through an incision and along a body passage until the balloon is located within the desired site. The term "desired site" refers to the location in the patient's body currently selected for treatment by a health care professional. After the balloon is disposed within the desired site, it can be selectively inflated to press outward on the body passage at relatively high pressure to a relatively constant diameter, in the case of an inelastic or non-compliant balloon material.

This outward pressing of a constriction or narrowing at the desired site in a body passage is intended to partially or completely re-open or dilate that body passageway or lumen, increasing its inner diameter or cross-sectional area. In the case of a blood vessel, this procedure is referred to as angioplasty. The objective of this procedure is to increase the inner diameter or cross-sectional area of the vessel passage or lumen through which blood flows, to encourage greater blood flow through the newly expanded vessel. The narrowing of the body passageway lumen is called a lesion or stenosis, and may be formed of hard plaque or viscous thrombus.

Unfortunately, within approximately six months after angioplasty, the lumen at the angioplasty site may re-close or become narrow again. This phenomenon is called restenosis, and may occur in as many as 30–40% of percutaneous transluminal angioplasty patients.

Restenosis may require an additional procedure, such as another angioplasty, drug therapy treatment, or even surgery including bypass graft. It is of course desirable to prevent or limit the occurrence of restenosis, especially since some patients may not be preferred candidates for another interventional treatment.

In an effort to prevent restenosis, short flexible cylinders or scaffolds made of metal or polymers, referred to as a stent, may be permanently implanted into the vessel to hold the lumen open, to reinforce the vessel wall and improve blood flow. The presence of a stent tends to keep the blood vessel open longer, but their use may be limited by various factors, including size and location of the blood vessel, a complicated or tortuous vessel pathway, etc. Also, even a vessel with a stent may eventually develop restenosis.

Some stents are expanded to the proper size by inflating a balloon catheter, referred to as "balloon-expandable" stents, while others are designed to elastically resist compression in a "self-expanding" manner. Both balloon-expandable stents and self-expanding stents are generally crimped or compressed to a diameter during delivery that is smaller than the eventual deployed diameter at the desired site. When positioned at the desired site within the lesion, they are deployed by inflating a balloon or being allowed to self-expand into the desired diameter.

Friction forces may tend to cause a crimped stent to slip in a proximal direction while the catheter system is advanced, or to slip in a distal direction if the physician decides to withdraw the stent without deploying it. It is of course desirable to retain the stent in the proper position, during advancement along a vascular path to the desired site.

Accordingly, it is an object of the present invention to provide balloon catheter systems for enhanced stent position retention during longitudinal movement of the catheter.

It is a further object of the present invention to provide methods for making balloon catheter systems having enhanced stent position retention.

These and various other objects, advantages and features of the invention will become apparent from the following description and claims, when considered in conjunction with the appended drawings.

BRIEF DESCRIPTION OF THE DRAWINGS

FIG. 4 is a longitudinal cross-section view of a balloon catheter and stent, according to the prior art;

FIG. 5 is a partial longitudinal cross-section view of a deflated balloon catheter and stent, arranged according to the principles of the present invention;

FIG. 6 is a partial longitudinal cross-section view of a partially inflated balloon catheter and stent;

FIG. 7 is a partial longitudinal cross-section view of a fully inflated balloon catheter and stent;

DETAILED DESCRIPTION OF THE PREFERRED EMBODIMENT

The following description of the preferred embodiments of the present invention is merely illustrative in nature, and as such it does not limit in any way the present invention, its application, or uses. Numerous modifications may be made by those skilled in the art without departing from the true spirit and scope of the invention.

Figure 1:
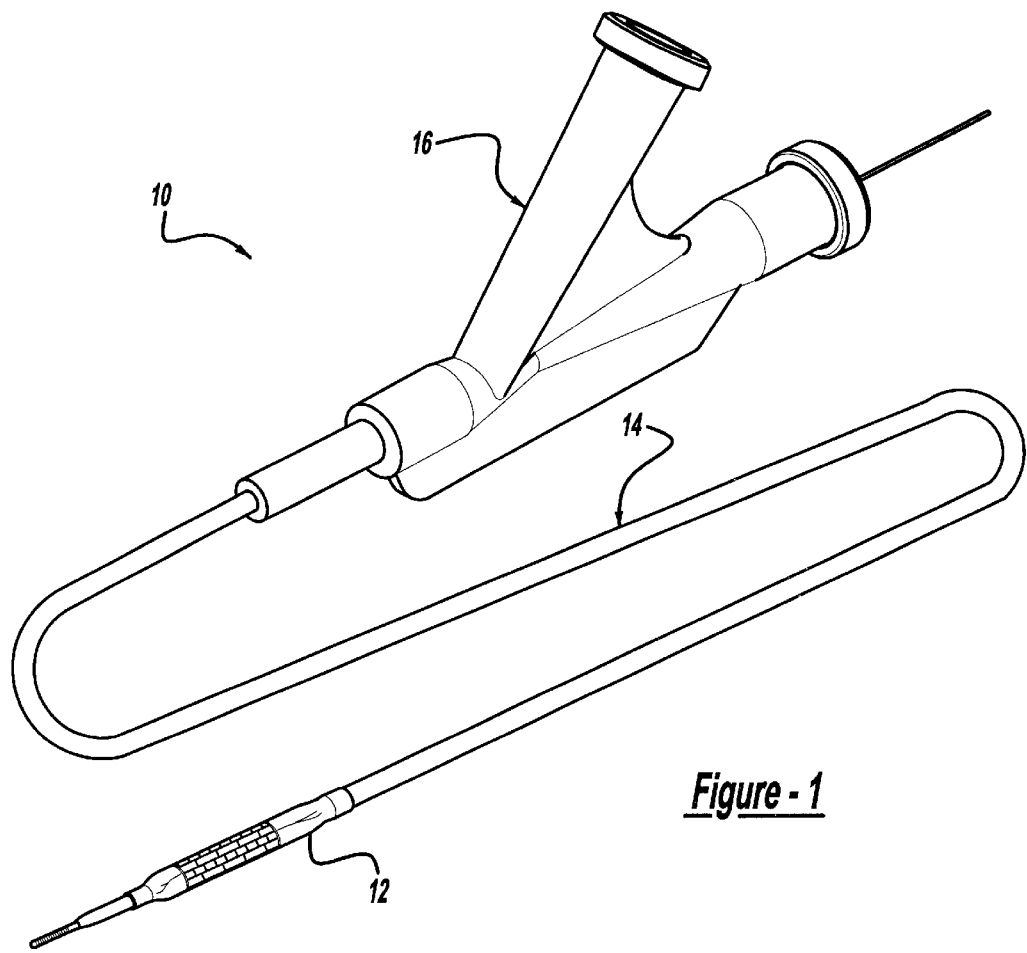
FIG. 1 is an external perspective view of a balloon catheter having a stent mounted around the balloon, arranged according to the principles of the present invention.
Figure 3:
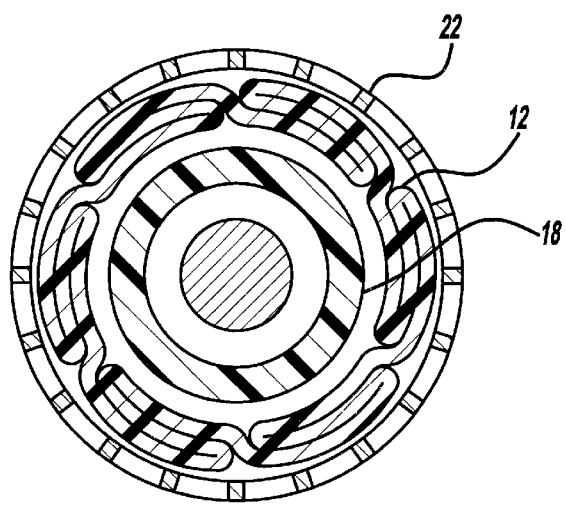
FIG. 3 is a transverse cross-section view of the balloon catheter and stent of FIG. 2, taken along line 3—3.
Figure 2:
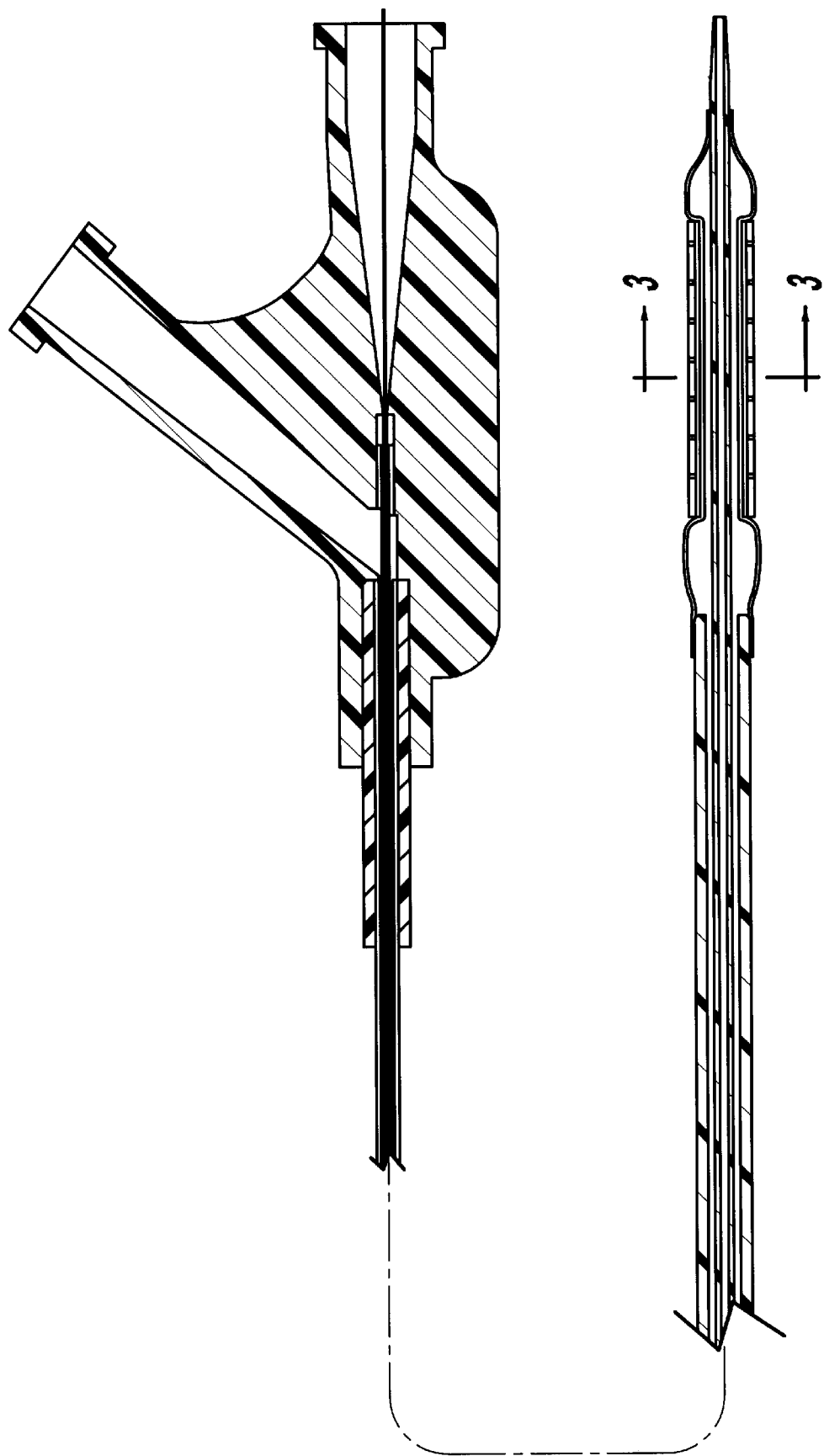
FIG. 2 is a longitudinal cross-section view of the balloon catheter and stent of FIG. 1.
Figure 8:
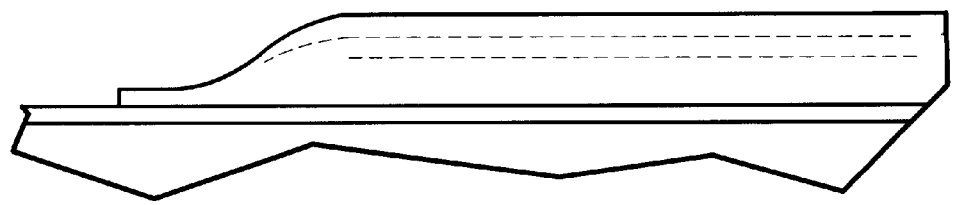
FIGS. 8–12 illustrate a method for making the balloon catheter stent delivery system of the present invention.
Figure 9:
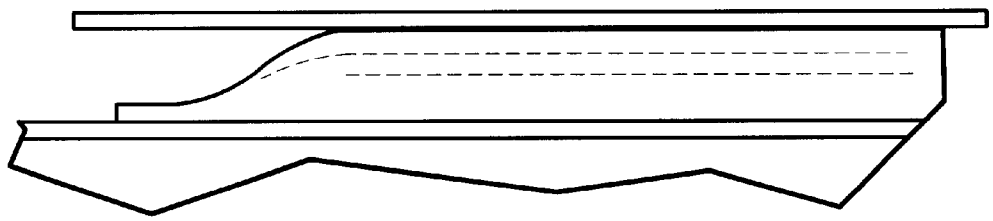
Figure 10:
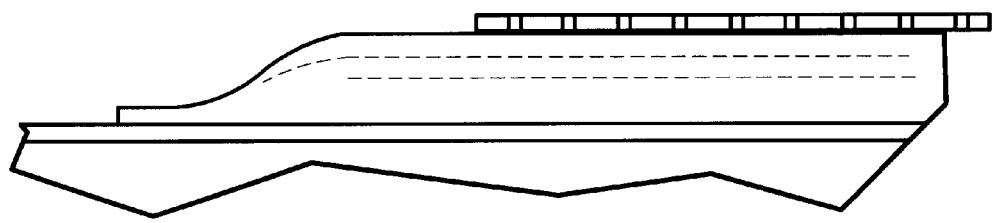
Figure 11:
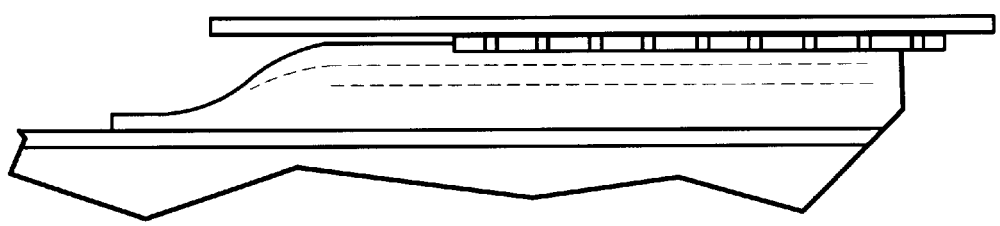
Figure 12:
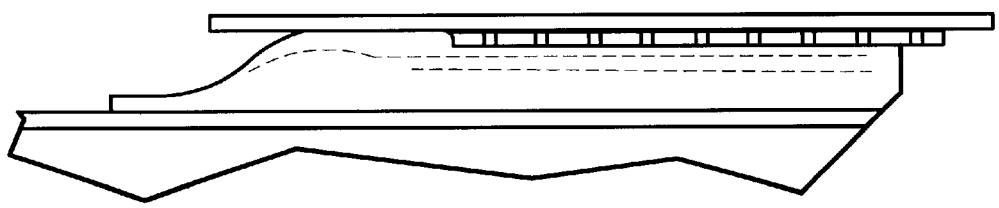

Referring to the drawings, a balloon catheter system is depicted, with one of the preferred embodiments of the present invention being shown generally at 10. The balloon catheter of FIG. 1 has an inflatable balloon 12, a relatively long and flexible tubular shaft 14, and a hub 16. The balloon is affixed to the shaft near a distal end of the shaft, and the hub is affixed to the proximal end of the shaft.

The shaft defines one or more passages or lumens extending through the shaft, at least one of which is an inflation lumen connected to the balloon for the purpose of selectively inflating and deflating the balloon. The inflation lumen thus provides fluid communication between the interior of the balloon at the distal end of the inflation lumen, and a hub inflation port having a coupling or luer-lock fitting at the proximal end for connecting the inflation lumen to a source of pressurized inflation fluid (not shown) in the conventional manner.

In the illustrated embodiment, the shaft is constructed of an inner and outer tubular body 18 and 20. The inner body defines a guidewire lumen, while the inflation lumen is defined by the annular space between the inner and outer tubular bodies. The guidewire lumen is adapted to receive an elongated flexible guidewire in a sliding fashion, such that the guidewire and catheter may be advanced or withdrawn independently, or the catheter may be guided along a path selected with the guidewire. The shaft may of course have various configurations instead of this coaxial design, including a single extruded tube defining any suitable number of parallel side-by-side lumens, a proximal shaft portion formed of a metal hypotube, and others.

The proximal hub is affixed to the proximal end of the shaft, and provides an inflation port and a guidewire port, again with a luer-lock fitting or hemostatic valve. Such a valve allows the guidewire to traverse and slide within the guidewire lumen, yet while resisting the loss of blood or other fluids through the guidewire lumen and guidewire port. As shown in the drawings, the inner and outer tubular bodies are securely received within the hub, and surrounded by a tubular strain relief. The hub provides fluid communication between the guidewire lumen and a guidewire coupling, as well as between the annular inflation lumen and the inflation coupling.

A stent 22 of any suitable type or configuration may be provided with the catheter of the present invention, such as the well-known Palmaz-Schatz balloon expandable stent. Various kinds and types of stents are available in the market, and many different currently available stents are acceptable for use in the present invention, as well as new stents which may be developed in the future. The stent depicted in the drawings is a cylindrical metal mesh stent having an initial crimped outer diameter, which may be forcibly expanded by the balloon to a deployed diameter. When deployed in a body passageway of a patient, the stent may be designed to preferably press radially outward to hold the passageway open.

As shown in the drawings, the balloon in its fully inflated profile shape has a cylindrical working portion with an inflated diameter located between a pair of conical end portions, and a pair of proximal and distal legs affixed to the shaft. The balloon in its deflated profile shape preferably has several pleats that are wrapped around the shaft. The balloon material is preferably substantially inelastic, and stretches a relatively small amount under pressures of 15 atmospheres or more. Various different materials may be used, including Nylon, PEEK, PEBAX material, or a block copolymer thereof.

The novel balloon catheter system of the present invention provides several advantages. Among these advantages is that the balloon has a composite profile shape which varies at different pressures. The balloon initially is in a deflated state and has a deflated profile shape, as specifically illustrated in FIG. 5, having a central bed portion with a deflated bed diameter being flanked by a pair of proximal and distal shoulders or puffs defining deflated shoulders or puffs diameters that are larger than the deflated bed diameter.

The balloon shoulders or puffs smoothly taper in proximal and distal directions respectively to proximal and distal legs that are affixed to the shaft. This deflated balloon profile shape thus provides a bed or nest portion for receiving the stent and tending to hold the stent in place, while minimizing friction or adverse contact between the ends of the stent and the blood vessel wall. The present invention thus tends to protect the leading or distal ends of the stent during advancement into the patient's body, and the proximal end of the stent during any withdrawal of the catheter system.

Figure 13:
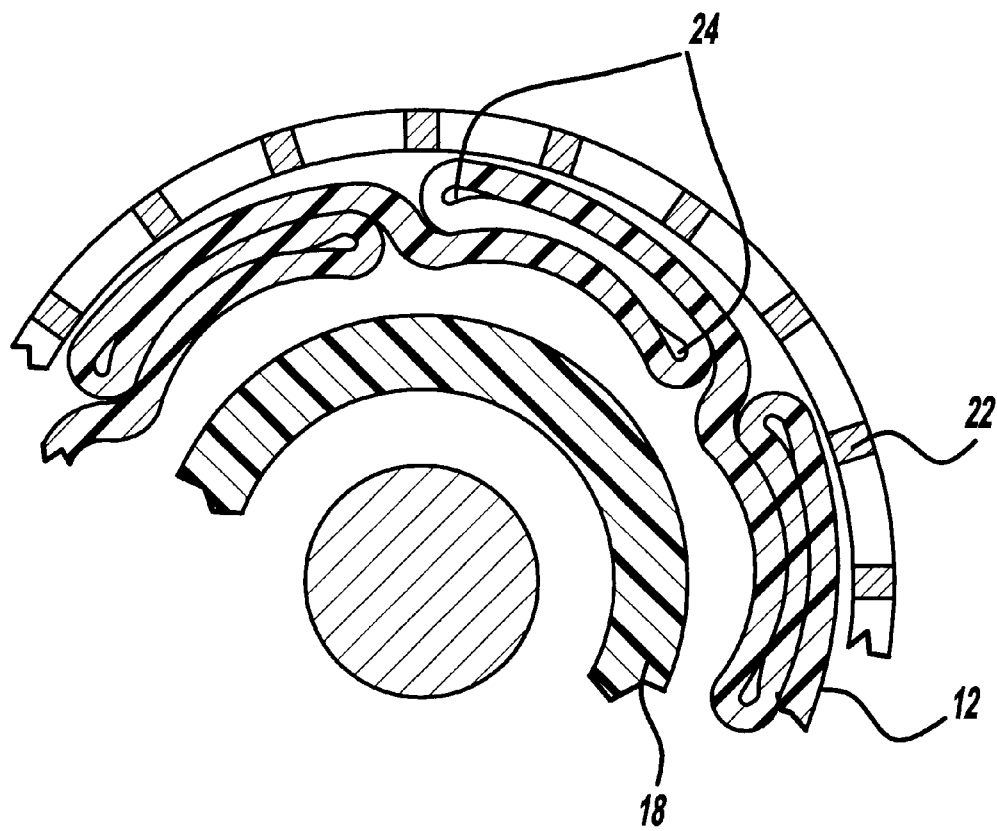
FIG. 13 is a partial transverse cross-section view of a stent mounted around a balloon defining small channels, arranged according to the present invention.

FIG. 13 shows small channels 24 that facilitate fluid communication from the proximal end of the balloon to the distal end, even when the balloon is deflated.

As specifically shown in FIG. 6, while the balloon is inflated at intermediate pressures, it will tend to exhibit nested profile shapes similar to the original deflated and nested profile shape of FIG. 5. One possible feature of the present invention is the formation of small channels that facilitate fluid communication from the proximal end of the balloon to the distal end, even when the balloon is deflated. The balloon thus tends to inflate more uniformly along its length, such that both proximal and distal balloon shoulders of puffs inflate at substantially the same times and pressures.

In addition, the present balloon catheter system can be modified to initiate partial inflation of the proximal and distal ends of the stent, to further resist longitudinal motion of the stent during inflation, and to facilitate more effectively fixing the stent in place within the blood vessel, called "tacking" the stent.

FIG. 7 depicts the balloon in its fully inflated profile shape. The stent bed shape disappears, and the balloon profile shape changes or morphs into a different profile shape when inflated at full inflation pressure. This fully inflated shape provides the preferable cylindrical working portion, wherein the portion of the balloon supporting and expanding the stent has an inflated diameter larger than any other portion of the balloon. This feature tends to prevent any part of the balloon from expanding excessively, which might cause local trauma to the blood vessel wall.

Accordingly, the portions of the present balloon reverse positions. The central bed portion initially has a smaller deflated diameter than the proximal and distal shoulders, which provides a desirably small outer maximum diameter for ease of insertion. The initial outer maximum diameter is referred to as the "primary profile." In contrast, the central balloon portion expands on full inflation to the largest diameter of the balloon, while the portions that previously formed the balloon shoulders expand comparably less. Indeed, the former pillows define the proximal and distal end conical portions of the fully inflated profile shape.

In the deflated shape, the balloon is therefore temporarily reformed into a different shape than what might conventionally result from simply deflating and pleating a previously known balloon. This temporarily reformed shape enhances stent position retention, and yet exhibits the preferable fully inflated shape. The balloon of the present invention also tends to reduce the maximum profile diameter after the balloon is deflated, referred to as the "secondary profile."

Another advantage of the present invention is the absence of any type of physical collar or other retaining device within the balloon, or on the outer balloon surface, or mounted on the balloon catheter shaft, which might undesirably increase the primary and/or secondary profiles of the stent delivery system.

One possible feature of the catheter system is that the balloon may be pleated in a particular pattern when deflated, whereby the central bed portion of the balloon that carries the stent has a greater number of pleats than the proximal and distal balloon shoulders.

The balloon catheter system of the present invention may be made using any of the following methods, as well as various modifications that will be apparent to those skilled in the art. The balloon is folded into any suitable or preferable number of longitudinal pleats which are wrapped around a portion of the catheter shaft, either manually or by using a pleating machine.

The balloon is then temporarily held in its pleated condition by slipping a forming tube in the proximal direction onto the pleated balloon, while the assembly is transported to the next processing station. The pleated balloon may be allowed to sit overnight, which may improve its tendency to hold its pleated shape. After the forming tube is removed, a stent is slipped onto the pleated balloon. The stent is then gently crimped or compressed around the balloon, with the pleats intact, to a crimped condition in which the stent has a crimped outer diameter.

The resulting balloon catheter and stent assembly is then placed in a tubular mold, having an internal diameter slightly greater than the crimped outer diameter of the stent. The tubular mold should have a constant inner diameter, to cause the balloon shoulders to have the preferred shape and diameter.

The balloon is then pressurized by applying a pressurized fluid or gas to the inflation port and through the inflation lumen. The preferred pressure of the inflation within the tubular mold may slightly exceed the rated burst pressure of the balloon, and the mold will prevent expansion of the stent while allowing the proximal and distal balloon shoulders to form. The pressurized fluid may preferably be dry nitrogen, and the pressure may preferably be maintained for a preselected period of time, such as several minutes.

While mold with the accompanying balloon catheter and stent assembly is held under pressure, they are then held in a hot liquid bath, for several purposes. First, the heat tends to set the stent in place, thus forming the desired proximal and distal shoulders. Second, if the balloon is made of Nylon according to one of the preferred embodiments, the water of the heating bath tends to hydrate the Nylon plasticizer of the balloon material. Of course, a hot air system or other heat source may also be used. The preferred temperature of the heated water bath is preferably below the permanent deformation temperature of the balloon material, and the time and pressure of this process may be extended to ensure that such a temperature will result in the desired composite shape and temporary reformation of the balloon.

The balloon, stent and mold assembly is then removed from the heated liquid bath, while the pressure is maintained for a period of time. After the pressure is relieved, the mold is then removed, and the balloon and stent assembly may be dried and again heated by applying a hot air gun for a period of time.

Several features of this preferred method of making the balloon catheter stent delivery system of the present invention have some importance to the performance of the resulting product, including the temperatures, pressures, time periods, crimped outer diameter of the stent, the internal diameter of the mold, as well as the thermal characteristics of the balloon, stent and mold.

The particular preferred method described above for making a balloon catheter stent delivery system obviously produces a balloon catheter having an already mounted stent. However, the methods of the present invention may also be used to produce a balloon catheter having the desired enhanced stent retention capability, without incorporating an included stent. Accordingly, the physician may then install and manually crimp any selected stent having the proper dimensions, while yet taking advantage of the enhanced stent position retention of the present invention. Also, this modified method of making the balloon of the present invention may be modified to produce balloon shoulders that have a greater initial outer diameter than that of the stent.

Accordingly, a balloon catheter having enhanced stent position retention may be made, without requiring a stent during the process, by a method similar to that described above. During this modified method, the presence of a stent is obviated by replacing it with a 'phantom stent' . One advantage of using a phantom stent is that it costs much less than an actual metal stent. Such a phantom stent may be formed of any suitable plastic material capable of withstanding the temperatures and pressures of the manufacturing method without melting or deforming. Suitable plastic materials for the phantom stent may thus include for example, PTFE or polyethylene.

Since the plastic phantom stent will not crimp in the same way that an actual metal stent does, it must be provided with a longitudinal slit or preferably a spiral cut. The phantom stent may thus be installed onto the pleated balloon, and removed after forming the stent nest with the accompanying shoulders by way of the cut in the plastic material.

When a balloon catheter is made and processed according to the methods of the present invention, and then the phantom stent is removed, the resulting balloon catheter has a stent nest or bed portion which will provide enhanced stent position retention for any stent of suitable dimensions.

Indeed, the size of the resulting balloon shoulders may be tailored by carefully selecting the tubular wall thickness of the plastic phantom stent to be greater than the wall thickness of the stent.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. A balloon catheter stent deployment system, comprising:

a balloon catheter with an elongated flexible shaft having proximal and distal ends, a hub affixed to the shaft proximal end and having an inflation port, and an inflatable balloon affixed to the shaft near the shaft distal end; the shaft defining an inflation lumen providing fluid communication of an inflation fluid between the hub inflation port and the balloon, such that the balloon is adapted for selective inflation from a deflated state to an inflated state, as well as later deflation; the balloon being formed of a substantially inelastic material; the balloon having a cylindrical working portion with an inflated cross-sectional area located between a pair of conical portions and a pair of leg portions when the balloon is in the inflated state; the balloon being initially in the deflated state having multiple longitudinal pleats;

an expandable tubular mesh stent defining a tubular wall thickness, mounted around the balloon and being crimped in an initial state to an initial outer diameter defined by an outer surface of the stent; the stent having substantially no tendency to self-expand absent an expansive force caused by inflating the balloon;

wherein the balloon in its deflated state defines a first and second pillow located immediately proximal and distal of the stent; each balloon pillow in an initial deflated state having an initial outer diameter equal to at least the initial outer diameter of the stent, thereby tending to frictionally retain the stent in an initial longitudinal position while the catheter system is advanced or withdrawn along a vascular path; such that the balloon defines an indented bed shape for the stent in the deflated state; and a plurality of small channels defined by folds at the outer ends of the balloon pleats in the initial deflated state; the channels extending generally in a longitudinal direction and facilitating fluid communication from a portion of the balloon interior within the proximal balloon pillow to a portion of the balloon interior within the distal balloon pillow, such that the balloon tends to inflate at its proximal and distal ends in a substantially simultaneous manner; wherein inner and outer portions of the balloon adjacent to each fold define a gap, the gap being between the fold and adjacent inner and outer portions of the balloon that are in contact with each other in at least one location, so as to clearly define the channels;

wherein the balloon is adapted to inflate and expand the stent to a deployed larger diameter, whereby the balloon forms said cylindrical working portion at above a preselected transition pressure, such that the cylindrical working portion and the portions defining the balloon pillows in the deflated state have substantially the same diameter in the inflated state; thereby causing said indented bed shape to substantially disappear.

2. The balloon catheter stent deployment system of claim 1, wherein said stent is formed of an integral unitary metal cylinder having a plurality of apertures for allowing the stent to expand from the initial diameter to the deployed diameter.

3. The balloon catheter stent deployment system of claim 1, wherein said balloon is formed of a material selected from the group consisting of Nylon, PEEK, or a block copolymer thereof.

4. The balloon catheter stent deployment system of claim 1, further comprising a second plurality of small channels defined by folds at inner ends of the pleats.

* * * * *

UNITED STATES PATENT AND TRADEMARK OFFICE
CERTIFICATE OF CORRECTION

PATENT NO.   : 6,464,718 B1
DATED        : October 15, 2002
INVENTOR(S)  : Jay F. Miller and Edward J. Play It is certified that error appears in the above-identified patent and that said Letters Patent is hereby corrected as shown below:

<u>Column 4,</u>
Line 40, "of puffs", should read -- or puffs --

Signed and Sealed this

Eighteenth Day of March, 2003

JAMES E. ROGAN
*Director of the United States Patent and Trademark Office*